United States Patent [19]

Mattson

[11] 4,233,977
[45] Nov. 18, 1980

[54] CLOSURE MEANS FOR COLLECTION APPLIANCES

[75] Inventor: Larry J. Mattson, Largo, Fla.

[73] Assignee: Howmedica, Inc., New York, N.Y.

[21] Appl. No.: 974,275

[22] Filed: Dec. 28, 1978

[51] Int. Cl.³ .............................................. A61F 5/44
[52] U.S. Cl. .................................................. 128/283
[58] Field of Search ............................. 150/6, 7, 8, 5; 128/275, 86 C, 77, 283

[56] References Cited

U.S. PATENT DOCUMENTS

| | | | |
|---|---|---|---|
| 2,877,768 | 3/1959 | Higgins | 128/283 |
| 3,618,606 | 11/1971 | Brown et al. | 128/283 |
| 3,655,118 | 4/1972 | Rinecker | 150/3 |
| 3,780,739 | 12/1973 | Frank | 128/283 |

FOREIGN PATENT DOCUMENTS

1370622 10/1974 United Kingdom.

*Primary Examiner*—Robert W. Michell
*Assistant Examiner*—Thomas Wallen
*Attorney, Agent, or Firm*—Francis X. Murphy; Charles J. Knuth; Lawrence C. Akers

[57] ABSTRACT

A novel closure means for an opening of a body eliminations or secretions collection appliance is disclosed. Said closure means comprises a semi-rigid strip securely affixed adjacent to one of the walls of the collection appliance. The opening is closed by lap folding the extremity of the collection appliance upon itself and then tucking the folded extremity into a gap between said strip and said wall. The novel closure means is particularly well suited for releasable closure of the drainage opening of an ostomy collection appliance.

10 Claims, 6 Drawing Figures

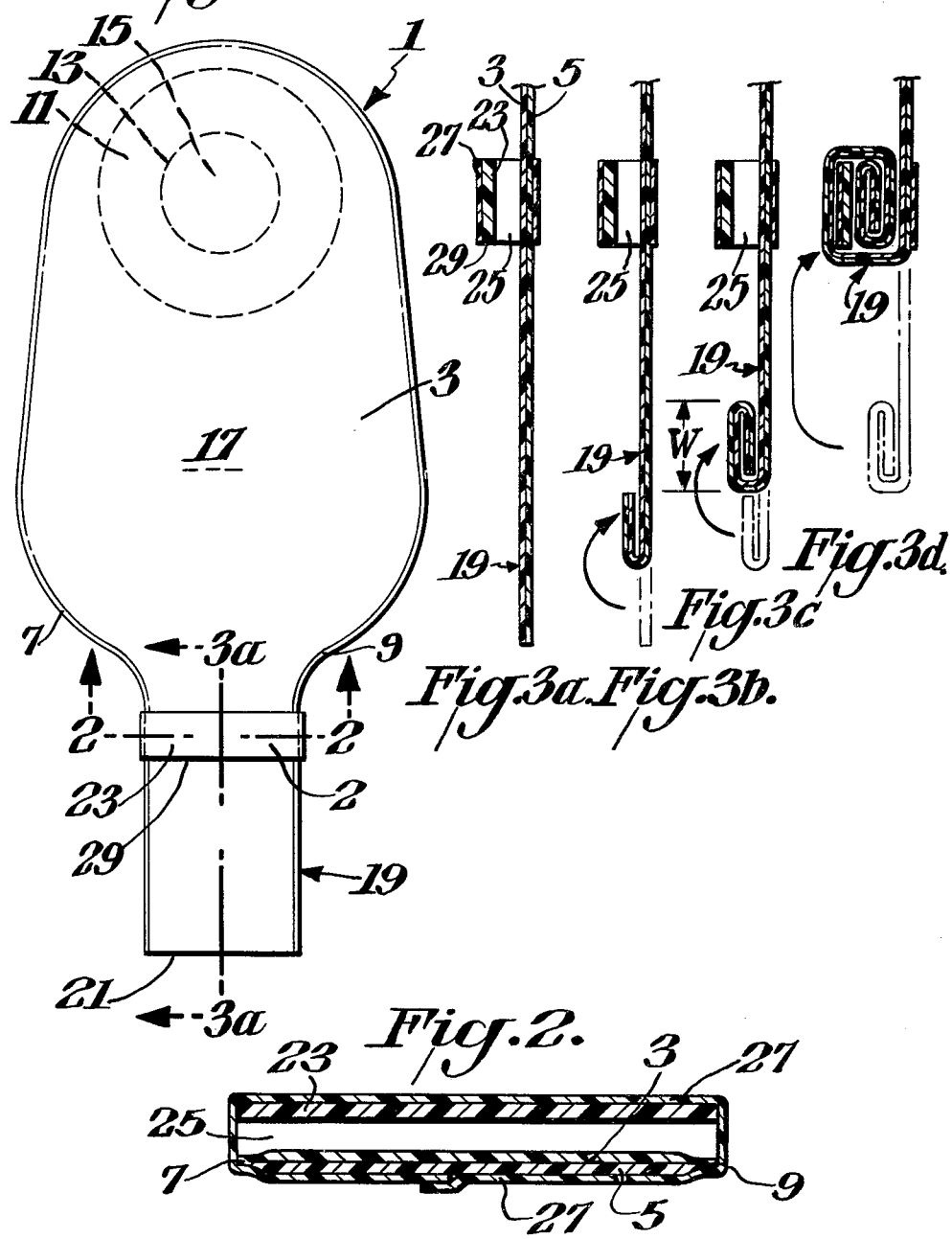

CLOSURE MEANS FOR COLLECTION APPLIANCES

BACKGROUND OF THE INVENTION

Portable ostomy collection appliances are widely used for the collection of fecal matter from patients who have undergone surgical procedures such as ileostomy or colostomy operations. A particularly useful type of collection appliance is formed with at least two opposed flexible flat walls joined together, e.g. by heat sealing, to define a fecal receiving chamber. Such appliances contain, of course, an opening in the wall facing the patient for receiving the stoma and means to secure the appliance to the body of the patient for portable use. The opposed flexible walls may be left unjoined to define a drainage opening at the bottom of the appliance, thus permitting the patient to drain the appliance without removing it from his body and thereby to use the same bag many times over before replacement. Drainage is faciliated by reducing the width of the appliance at its lower portion to form a tail spout through which drainage readily occurs.

The drainage opening of an ostomy collection appliance, with or without a tail spout, must be capable of being readily opened and closed by the patient for and after drainage and must of course remain securely closed when the appliance is not being drained. A variety of drainage opening closure means for ostomy collection appliances are known to the art. Certain drainage opening closure means such as rubber bands, metal clips, wires, etc., are not securely affixed to the collection appliance and thus may be misplaced by the patient. Certain other types of drainage opening closure means securely affixed to the appliance are known to the art, but generally possess one or more of the disadvantages of being heavy, bulky, undependable, or difficult or inconvenient to use.

It is an object of this invention to provide a lightweight non-bulky ostomy collection appliance drainage opening closure means which is securely affixed to the appliance, can be used by the patient with maximum ease and comfort, and provides a highly dependable seal against accidental drainage or leakage. Other objects will be apparent from a reading of the specification and claims herein.

SUMMARY OF THE INVENTION

A novel means for releasably closing the drainage opening of an ostomy collection appliance of the type having at least front and back opposed flexible flat walls, said walls defining a fecal receiving chamber between them and terminating at said drainage opening at the bottom of said appliance, has now been invented. The novel drainage opening closure means comprises a semi-rigid strip securely affixed adjacent to one of said opposed flexible walls above said drainage opening so as to leave a gap between said semi-rigid strip and said adjacent flexible wall, whereby the structure and position of said drainage opening closure means is such that said drainage opening may be releasably closed by folding the lower ends of said opposed walls upwardly upon themselves together, and tucking said folded ends downwardly into said gap for snug fit therein. The novel drainage opening closure means of the invention is easy and convenient to use, and contains no separate pieces of equipment such as snaps, clips, wires or rubber bands that can break or fail or be misplaced by the patient. A substantially more positive seal is attained against the semi-rigid strip than against elastic bands or other stretchable material, with said seal being improved as more pressure is applied to it, i.e., as the appliance becomes more full. The novel closure means is highly resistant in the closed position to undesired leakage or drainage, and to unexpected opening due to motion or jarring. It is highly suitable for use, linkage many prior art closures, when the opposed flexible flat walls of the appliance are each less than 4 mils thick, as is the case in certain recently developed appliances. The novel drainage opening closure means has a very low profile to conceal the presence of an ostomy collection appliance. Also, the closure means of the invention has no structure (e.g. pockets) which can trap water during bathing or trap and collect excrement. Preferably, the flexible wall adjacent to which the semi-rigid strip is securely affixed faces away from the body of the patient in use so as to facilitate opening and closing of the appliance by the patient.

The drainage opening closure means of the invention may be used in ostomy appliances whose opposed walls do not form a tail spout (see, e.g., U.S. Pat. No. 2,703,576), but is particularly well suited for use in ostomy collection appliances which do possess a tail spout terminating at the drainage opening. In a preferred embodiment of the invention, the semi-rigid strip is securely affixed to the upper portion of a tail spout and the lower ends of the opposed flexible walls are folded together upwardly upon themselves at least twice before being tucked downwardly into said gap to achieve said closure, with the fold width being about equal to the width of said strip. In this preferred embodiment, the distance of the semi-rigid strip above the drainage opening is established by the width of said strip and the number of folds contemplated before tucking.

As broadly contemplated, the invention herein can be incorporated into body eliminations or secretions collection appliances other than ostomy collection appliances, e.g. weeping lymph gland fluid, bile, and would drainage collection appliances, and can be used for the releasable closure of openings other than drainage openings, e.g. irrigation and gas venting openings not necessarily at the bottom of the appliance. The collection appliance may possess only front and back opposed flexible flat walls (see FIGS. 1 to 3 herein) or may possess additional opposed flexible walls as in the gusseted bag disclosed in U.S. Pat. No. 2,703,576. The opposed walls may be joined together from separate sheets, e.g. by gluing or heat sealing, or may be formed from a unitary piece, e.g. by flattening a unitary piece of tubing. The opposed flexible flat walls are typically, but not necessarily, made of polymeric material. Thus, for example, said walls could also be made of waterproof non-woven cloth. The semi-rigid strip is preferably, but not necessarily, made of plastic. Thus, for example, said strip could also be made of waxed cardboard.

DETAILED DESCRIPTION OF THE INVENTION

The invention will be described in detail with reference to a preferred embodiment thereof, which is an ostomy collection appliance having a tail spout. Reference to this embodiment does not limit the scope of the invention, which is limited only by the scope of the claims. In the drawings:

FIG. 1 is a front plan view of an ostomy collection appliance having a drainage opening closure means of the invention;

FIG. 2 is an enlarged section view taken along line 2—2 of FIG. 1; and

FIGS. 3a to 3d are enlarged section views taken along line 3a–3a of FIG. 1 showing the sequence of folding and tucking involved in closing the drainage opening of the appliance of FIG. 1.

A preferred embodiment of the invention, i.e. an ostomy collection appliance 1, is shown in FIGS. 1 to 3. Appliance 1 comprises front and back opposed flexible flat walls of polymeric material 3 and 5 sealed together by heat sealing of their outside edges as at 7 and 9. Flexible flat polymeric circular collar 11, heat sealed at its inner edge 13 to wall 5 and concentric with circular stoma-receiving opening 15 in wall 5, is utilized to secure appliance 1 to the body of the patient or a suitable faceplate by known means, for example with the use of an appropriate adhesive, for portable use. Walls 3 and 5 define between them a fecal receiving chamber 17 and a tail spout 19, also referred to herein as a drain spout. Walls 3 and 5 are left unsealed at their lower edges, thereby defining drainage opening 21.

The drainage opening closure means of appliance 1 comprises a semi-rigid strip of plastic material 23 securely affixed adjacent to wall 3 at the upper portion of tail spout 19. Strip 23 is secured in such a way as to leave a gap 25 between strip 23 and adjacent wall 3. As shown in FIG. 2, strip 23 is secured to wall 5 by means of a piece of flexible single-sided pressure-sensitive tape 27 adhering to the surfaces of strip 23 and wall 5 facing away from gap 25. Use of tape 27 as shown in FIG. 2 introduces no stress points to wall 5 in the region of attachment of tape 27 thereto. Alternate methods of securing strip 23 to wall 5 and/or wall 3 may, of course, be employed, such as welding or use of an adhesive placed at the ends of said strip.

As used in this application, the term "securely affixed" means that the semi-rigid strip remains secured in place during drainage, and thus cannot be misplaced by the patient. If, however, it is desired to remove said semi-rigid strip from position, for example to introduce some different sort of drainage opening closure means, such removal can be easily accomplished without damage to tail spout 19 by simply peeling away the piece of tape 27.

Flexible flat walls 3 and 5 may be made from a wide variety of polymeric materials well known to the collection appliance art, e.g. polyethylene and polymers of the vinyl and saran families, and are, for example, each about 3 mils in thickness. Flexible tape 27 may be about 5 mils in thickness and made of plastic, e.g. polypropylene. Strip 23 is, for example, a 0.025 inch thick strip of polypropylene or polystyrene. Strip 23 is consequently far stronger than walls 3 and 5. As used in this application, the term "semi-rigid" refers to a piece of material intermediate in rigidity between a metal (e.g. steel) strip and a common rubber band. Insufficient rigidity gives rise to an inadequate seal against undesired drainage, leakage or opening, while excessive rigidity would unnecessarily introduce the risk of injury to a patient falling upon the end of the strip, which would not buckle because of its excessive rigidity. Whether or not a piece of material is semi-rigid depends, of course, both upon its dimensions and the material of which it is constructed.

By way of example only, semi-rigid strip 23 of appliance 1 is 5.4 cm. long and 1.5 cm. wide. Lower edge 29 of strip 23 is situated 6.4 cm. above drainage opening 21. The substantial width of strip 23 provides a far greater sealing area than that provided by the known elastic band and metal clip drainage opening closure devices of the prior art.

The easy and convenient operation of a closure means of this invention is illustrated in FIGS. 3a to 3d. The fully opened ostomy collection appliance is shown in FIG. 3a. To close the drainage opening, the lower ends of walls 3 and 5 are folded together upwardly upon themselves a first time (see FIG. 3b) and then a second time (see FIG. 3c), with the fold width W being about equal to the width of semi-rigid strip 23. Said lower ends are then folded upwardly above semi-rigid strip 23 and tucked securely downwardly into gap 25 for snug fit therein to achieve the closure of drainage opening 21 (see FIG. 3d). This combined folding and tucking operation is very easy and convenient to perform, and does not involve any difficult or frustrating operation such as threading tail spout 19 through a metal clip or elastic band.

To release the drainage opening closure means and drain the ostomy collection appliance 1, the procedure illustrated in FIGS. 3a to 3d is simply reversed. Even though semi-rigid strip 23 remains secure in position during drainage, it does not constrict tail spout 19 or act in any other way to interfere with the drainage operation.

I claim:

1. In an ostomy collection appliance of the type having at least front and back opposed flexible flat walls, said walls defining a fecal receiving chamber between them and terminating at a drainage opening at the bottom of said appliance, and means for releasably closing said opening, the improvement wherein
said drainage opening closure means consists essentially of a semi-rigid strip securely affixed transversely with respect to the collection appliance, in spaced relation to said drainage opening and adjacent and parallel to one of said opposed flexible walls so as to leave a gap between said semi-rigid strip and said adjacent flexible walls, said gap being open at both the top and bottom thereof,
whereby said drainage opening may be releasably closed by folding the lower ends of said opposed walls upwardly upon themselves together, and tucking said folded ends downwardly into said gap for snug fit therein.

2. The improvement of claim 1 wherein said opposed flexible flat walls define additionally a tail spout terminating at said drainage opening, said semi-rigid strip is securely affixed to said tail spout, and said lower ends of said opposed walls form a substantial portion of said tail spout.

3. The improvement of claim 2 wherein said semi-rigid strip is securely affixed to the upper portion of said tail spout and said lower ends of said opposed walls are folded together upwardly upon themselves at least twice before being tucked downwardly into said gap to achieve said closure, with the fold width being about equal to the width of said strip.

4. The improvement of claims 1 or 2 wherein said flexible wall adjacent to which said strip is securely affixed faces away from the body of the patient in use.

5. The improvement of claim 4 wherein said semi-rigid strip is securely affixed to the flexible wall facing toward the body of the patient in use.

6. The improvement of claim 5 wherein said strip is securely affixed to said flexible wall by means of flexible single-sided pressure-sensitive tape adhering to the surfaces of said strip and said wall facing away from said gap.

7. The improvement of claim 6 wherein said semi-rigid strip is made of plastic.

8. The improvement of claim 1 wherein each of said opposed flexible flat walls is made of polymeric material.

9. The improvement of claim 8 wherein each of said opposed flexible flat walls is less than 4 mils in thickness.

10. The improvement of claims 1, 2, or 8 wherein said semi-rigid strip is made of plastic.

* * * * *